United States Patent [19]

Litman et al.

[11] Patent Number: 4,540,659

[45] Date of Patent: Sep. 10, 1985

[54] SIMULTANEOUS CALIBRATION HETEROGENEOUS IMMUNOASSAY

[75] Inventors: David J. Litman, Mountain View; Edwin F. Ullman, Atherton, both of Calif.

[73] Assignee: Syva Company, Palo Alto, Calif.

[21] Appl. No.: 399,107

[22] Filed: Jul. 16, 1982

Related U.S. Application Data

[63] Continuation-in-part of Ser. No. 255,022, Apr. 17, 1981, Pat. No. 4,391,904, which is a continuation of Ser. No. 106,620, Dec. 26, 1979, Pat. No. 4,299,916.

[51] Int. Cl.$^3$ .................... G01N 33/54; C12N 9/96
[52] U.S. Cl. ........................ 435/7; 435/188; 436/524; 436/525; 436/527; 436/529; 436/531; 436/824
[58] Field of Search ............ 435/4, 7, 188, 810, 435/805; 436/524, 525, 527, 528, 529, 531, 546, 808, 810, 824; 422/55, 56, 61

[56] References Cited

U.S. PATENT DOCUMENTS

4,294,817 10/1981 Burgett .................................. 435/5
4,315,907 2/1982 Fridlender et al. ................... 435/7
4,331,650 5/1982 Brewer et al. ........................ 422/56
4,366,241 12/1982 Tom et al. ............................ 435/810

*Primary Examiner*—Esther M. Kepplinger
*Attorney, Agent, or Firm*—Theodore J. Leitereg; Bertram I. Rowland

[57] ABSTRACT

An assay method and compositions are provided for determining the presence of an analyte in a sample. The analyte is a member of an immunological pair (mip) comprising ligand and receptor. By providing a first measurement surface capable of specifically binding a labelled reagent in an amount depending upon the presence of analyte in the sample and a second calibration surface capable of binding a second labeled reagent in a manner unaffected by the presence of analyte in the sample, calibration of individual tests can be accomplished simultaneously with the performance of the test itself. A signal producing system includes an enzyme, a catalyst usually bonded to a mip which defines the first labeled reagent for binding to the measurement surface and the same catalyst conjugated to a ligand capable of binding to the calibration surface. Preferably, both labeled reagents have the same composition and the calibration surface includes anti-(first catalyst).

4 Claims, No Drawings

SIMULTANEOUS CALIBRATION HETEROGENEOUS IMMUNOASSAY

CROSS-REFERENCE TO RELATED APPLICATION

This application is a continuation-in-part of application Ser. No. 255,022, filed April 17, 1981, now U.S. Pat. No. 4,391,904 which application is a continuation of application Ser. No. 106,620 filed Dec. 26, 1979, now U.S. Pat. No. 4,299,916 issued Nov. 10, 1981.

BACKGROUND OF THE INVENTION

1. Field of the Invention

There is continuing interest in developing new, simpler and more rapid techniques to detect and measure the presence of an analyte in a sample. The analyte may be any of a wide variety of materials, such as drugs, naturally occurring physiological compounds, pollutants, chemicals, contaminants, or the like. In many cases, speed is important for the measurement, particularly with certain physiologically active compounds. In other situations, convenience can be a major consideration.

One convenient and rapid technique which has found wide application is the use of a "dip stick," generally comprising a solid rod or film which can be dipped in a sample and subsequently processed to produce a signal based on the amount of analyte in the original sample. There is ample instrumentation to measure a signal, such as light absorption, reflectance or fluorescence, of a compound bound to a solid surface. Also the dip stick allows for convenient handling, transfers, separations, and the like.

Although convenient, such techniques are highly sensitive to development time, temperature, interfering factors, reagent stability and other conditions which may affect the level of the observed signal. In performing quantitative assays where the observed signal is compared to a standard, it is necessary that the test conditions be carefully controlled to match those of the standard. Such careful control, however, detracts from the convenience of the dip stick, increases the time and cost of performing the assays, and uncertainty of the result. Moreover, the presence of interfering factors in the sample and instability of reagents are difficult to overcome even with the greatest of care.

It is therefore desirable to develop a new assay technique which provides for accurate detection of an analyte in a sample and which is largely insensitive to development time, temperature, interfering factors in the sample, reagent stability and the like.

2. Brief Description of the Prior Art

Patents concerned with various immobilized reagents and different types of test strips include U.S. Pat. Nos. 3,993,451; 4,038,485; 4,046,514; 4,129,417; 4,133,639; and 4,160,008, and German Offen. No. 2,636,244. Patents disclosing a variety of methods involving separations of bound and unbound antigen include U.S. Pat. Nos. Re. 29,169; 3,949,064; 3,984,533; 3,985,867; 4,020,151; 4,039,652; 4,067,959; 4,108,972; 4,145,406; and 4,168,146.

SUMMARY OF THE INVENTION

Apparatus and methods are provided for determining the presence of analyte in a sample suspected of containing the analyte. The method and apparatus involve first and second surfaces, referred to as measurement and calibration surfaces, each involving a signal producing system desirably having at least one catalyst and one substrate, where the systems are substantially the same and involve at least one common member of the signal producing system.

The measurement surface involves the binding of a conjugate to the surface by means of specific binding pair complex formation, where the conjugate comprises a member of the signal producing system ("sps member") bound to a member of a specific binding pair. The amount of conjugate which binds to the surface is related to the amount of analyte in the assay medium.

The calibration surface has a sps member bound to the surface, either covalently or non-covalently, either initially or through the intermediacy of specific binding pair complex formation, where the specific binding pair is different from the binding pair of the measurement surface.

By comparison of the level of signal generating compound at each surface, one can determine whether the amount of analyte is greater or lesser than a predetermined amount, which amount is indicated by the signal generated from the calibration surface.

DESCRIPTION OF THE SPECIFIC EMBODIMENTS

In accordance with the subject invention, an assay method and apparatus are provided for determining an analyte in a sample suspected of containing said analyte, by introducing together at least two different surfaces into a liquid assay medium, where one surface is referred to as the measurement surface and the other surface is referred to as the calibration surface. The assay involves the use of a signal producing system, desirably having at least one catalyst, usually an enzyme, and at least one substrate.

In order to obtain amplification of the signal it is desirable that for each binding event of analyte to its homologous binding pair member, there be a plurality of signal producing events. The plurality may be as a result of a dynamic or static system. In the dynamic system a catalyst is employed, usually an enzyme, and the signal producing system includes at least one substrate, normally a coenzyme, where either the enzyme or substrate may be bound to the specific binding pair member. Where the substrate cannot be cycled, usually a plurality of substrate molecules will be bound to a hub to provide for a plurality of substrate molecules being involved with a single binding event.

Alternatively, one can bind a plurality of non-catalytic molecules which provide a detectable signal to a hub. Such molecules will usually be spectrophotometrically detectable. While dyes providing light absorption might be useful in some instances, fluorescers and chemiluminescers will ordinarily be used as providing a more accurately measurable signal with conventionally available equipment.

The amount of sps member present as a conjugate of the sps member and a specific binding pair member, which binds to the measurement surface through a specific binding pair complex, is related to the amount of analyte present in the medium. The amount of sps member bound to the calibration surface during the assay will provide a signal level for at least one, usually one, predetermined analyte concentration in the range of interest. The presence of the sps member on the calibration surface may be as a result of covalent or non-covalent binding, either prior to immersion into the sample containing assay solution or during the performance of the assay, except that for a non-catalytic sps member, binding will be non-covalent and subsequent to immersion.

The subject method and apparatus provide for simultaneous calibration of the assay system during the performance of each individual test. The signal producing system as it relates to the production of a detectable signal at the two surfaces is subject to a number of the same conditions which affect the observed detectable signal. Thus, variations in the production of a detectable signal, due to variations in conditions, endogenous materials in the sample, or the like, will affect the production of the detectable signal at the two surfaces in parallel ways, so that the signal level of the calibration surface may serve as a standard for the evaluation of the signal level of the measurement surface.

The present invention relies on having two surfaces, each employing a signal producing system which results in the production of a detectable product. The amount of sps member which binds to the measurement surface is related to the amount of analyte in the medium. The production of the detectable product which produces the signal on the surface will be directly related to the amount of the sps member to the measurement surface. By contrast, the amount of sps member which binds to the calibration surface will not be solely dependent upon, and is usually independent of, the amount of analyte in the medium. The amount of sps member available to the calibration surface, even when not prebound to the calibration surface, will usually be independent of the amount of analyte in the assay medium.

Once the sps member molecules are bound to the surfaces, the signal production at the two surfaces will be subject to the same environment, so that the production of a detectable signal on the calibration surface can be used as a basis for a qualitative or quantitative determination of the concentration of analyte in the medium. For the most part, with visual determinations, the calibration surface will not be used for determining a specific concentration, but rather for determining whether the analyte of interest is present at all or present in an amount greater than a predetermined level.

A wide variety of protocols and combinations can be employed in performing the assays and varying the materials bound to the two surfaces. It should be understood that in referring to two surfaces, more than two surfaces may be involved, where a plurality of one or both of the measurement and calibration surfaces are present in the apparatus.

The calibration surface can involve the initial binding of the sps member to the surface, except for non-catalytic systems, where a predetermined amount of catalyst is bound to the surface. Alternatively, a specific binding pair member may be employed on the calibration surface which binds to the sps member or a specific binding pair member bound to the sps member. Such specific binding pair member binds to a determinant site other than the determinant site involved in the binding of analyte to the specific binding pair member homologous to the analyte.

The measurement and calibration surfaces may be formed from any convenient material and may have any convenient structure, where the surface substantially retains its structural integrity during the assay. The two surfaces are normally juxtaposed, so as to be subject to the same environmental conditions to ensure that the sps member at the two surfaces responds in substantially the same way to the environmental conditions.

Various signal producing systems can be employed, which can be tailored to particular analytes or particular situations. In each case, the signal producing system will include at least one functionality capable of providing a detectable signal, desirably at least one catalyst, usually at least one enzyme, and at least one substrate with a catalyst sps, where the sps member will be bound to a specific binding pair member to form a conjugate which binds to at least the measurement surface and may bind to both the measurement surface and the calibration surface.

The apparatus containing the two surfaces will be contacted together with one or more solutions where the analyte and conjugate have had an opportunity to bind to the measurement surface and, as appropriate, to the calibration surface. For catalytic systems, as required, the two surfaces will be introduced into a reagent solution having the necessary substrates and cofactors for the signal producing system. In certain situations, however, for example, where two catalysts are employed, all of the signal producing system may be combined in combination with the sample in a single assay medium. After a predetermined time, the surfaces are removed from the development solution and the detectable signal on the measurement surface and the calibration surface compared.

The subject invention will now be described in greater detail. However, before describing the invention in detail, a number of terms will be defined.

Definitions

Analyte—the compound or composition to be measured, which may be a ligand, which is mono- or polyepitopic, usually antigenic or haptenic, a single or plurality of compounds which share at least one common epitopic or determinant site, or a receptor.

Specific binding pair ("mip")—two different molecules, where one of the molecules has an area on the surface or in a cavity which specifically binds to a particular spatial and polar organization of the other molecule. The members of the specific binding pair are referred to as ligand and receptor (antiligand). These will usually be members of an immunological pair, although other specifically binding pairs such as biotin-avidin, hormones-hormone receptors, and the like are not immunological pairs. Homologous or complementary substances are ligand and receptor, while analogous substances are either ligands or receptors, which are differentiated in some manner, e.g., labeling.

Ligand—any organic compound for which a receptor naturally exists or can be prepared.

Receptor (antiligand)—any compound or composition capable of recognizing a particular spatial and polar organization of a molecule, i.e., epitopic or determinant site. Illustrative receptors include naturally occurring receptors, e.g., thyroxine binding globulin, antibodies, enzymes, Fab fragments, lectins, nucleic acids and the like.

Ligand analog—a modified ligand which can compete with the analogous ligand for a receptor, the modification providing means to join a ligand analog to another molecule. The ligand analog will usually differ from the ligand by more than replacement of a hydrogen with a bond which links the ligand analog to a hub or label, but need not.

Poly(ligand analog)—a plurality of ligands or ligand analogs covalently joined together, normally to a hub nucleus. The hub nucleus is a polyfunctional material, normally polymeric, usually having a plurality of functional groups, e.g., hydroxy, amino, mercapto, ethylenic, etc., as sites for linking. The hub nucleus is normally water soluble or at least dispersible and will usually be at least about 35,000 daltons, but generally not exceeding about 600,000 daltons. Illustrative hub nuclei include polysaccharides, polypeptides, including proteins, nucleic acids, ion exchange resins and the like.

Surface—the measurement and calibration surfaces will each be non-dispersed and have an available surface area of at least about 50 $\mu m^2$ and generally greater, often at least about 1 $mm^2$, usually being on a common support, particularly when less than about 0.5 $cm^2$, and may be of any material which is insoluble in water and provides the necessary properties for binding of a mip and a detectable signal generating compound to provide a desired signal level. Desirably, the surface will be gelatinous, permeable, bibulous, porous or have a rough or irregular structure, which may include channels or indentations, generally having a substantial void volume as compared to total volume. Depending upon the nature of the detectable signal generating compound, the surface will be adsorbent or non-adsorbent, preferably being weakly or non-adsorbent. The surface may be transparent or opaque, a single material or a plurality of materials, mixtures or laminates. A wide variety of materials and shapes may be employed. The surface will be capable of substantially retaining its integrity under the conditions of the assay, so that substances which are bound to the surface will remain bound to the surface and not diffuse into solution. It is desirable that underlying structures of both the measurement and calibration surfaces be substantially identical.

Catalyst-bound-mip—catalyst, usually an enzyme, conjugated to a mip. The catalyst is a member of the signal producing system and the mip is chosen to bind to the measurement surface in accordance with the particular protocol.

Signal producing system ("sps")—the signal producing system may be catalytic or non-catalytic, preferably catalytic, more preferably having an enzyme catalyst; desirably two enzymes are employed, where the product of one enzyme is the substrate of the other enzyme; also included with a catalytic signal producing system will be at least one substrate and, as appropriate coenzyme(s). The signal producing system produces a detectable signal at the measurement surface related to the amount of analyte present in the medium and involves at least one ligand-receptor pair at the calibration surface e.g. ligand and natural receptor or antibody, enzyme and substrate or enzyme. The signal producing system, in whole or in part, produces a detectable signal at the calibration surface by means of a "signal generating compound" which binds to the surface and generates a detectable signal. The level of the detectable signal at the calibration surface is dependent on at least one factor independent of the amount of analyte. Other materials which may be included in the signal producing system are light for fluorescers, reactants for chemiluminescence and scavengers for an intermediate product, where at least two enzymes are employed.

As a shorthand, a member of the signal producing system will be referred to as an "sps member". The sps member may be a fluorescer, chemiluminescer, enzyme or substrate, where the term substrate includes a coenzyme.

METHOD

The subject assay is carried out in an aqueous zone or medium, where the final assay medium may be the result of prior individual additions of reagents or combinations of reagents and incubations, prior separations involving removal of the surfaces from an aqueous medium and transfer to a different aqueous medium having one or more reagents, or combinations thereof. While the subject method does not require a separation of labeled conjugate which is unbound from that which is bound to one or both surfaces through mip complexes, in many protocols a developer solution will be employed which is substantially free of unbound catalyst. The various media involved in the assay consist of a liquid phase and a solid phase which defines both the measurement and calibration "surfaces."

In carrying out the assay, the surfaces will be contacted by the sample, and by the members of the signal producing system, and any ancillary materials, in an aqueous medium, either concurrently or stepwise, to provide a detectable signal associated with the surfaces. The detectable signal at the measurement surface will be related to the amount of the labeled conjugate bound to that surface, which relates to the amount of analyte in the sample. Depending upon the nature of the signal producing system and the desired method for detecting the signal, the surfaces may be read in the assay medium or will be read separate from the assay medium.

In carrying out the assay, an aqueous medium will normally be employed. Other polar solvents may also be included, usually oxygenated organic solvents of from 1–6, more usually from 1–4 carbon atoms, including alcohols, ethers and the like. Usually these cosolvents will be present in less than about 40 weight percent, more usually in less than about 20 weight percent.

The pH for the medium will usually be in the range of about 4–11, more usually in the range of about 5–10, and preferably in the range of about 6.5–9.5. The pH is chosen so as to maintain a significant level of specific binding by the receptor while optimizing signal producing efficiency. In some instances, a compromise will be made between these two considerations. Various buffers may be used to achieve the desired pH and maintain the pH during the determination. Illustrative buffers include borate, phosphate, carbonate, tris, barbital and the like. The particular buffer employed is not critical to this invention but in individual assays, one buffer may be preferred over another.

Moderate temperatures are normally employed for carrying out the assay. Constant temperatures during the period of the measurement are generally not required, but rapid and large fluctuations are not desirable. The temperatures for the determination will generally range from about 10°–50° C., more usually from about 15°–45° C.

The concentration of analyte which may be assayed will generally vary from about $10^{-4}$ to $10^{-15}$M, more usually from about $10^{-6}$ to $10^{-13}$M. Considerations such as whether the assay is qualitative, semi-quantitative or quantitative, the particular detection technique and the concentration of the analyte of interest will normally determine the concentration of the other reagents.

The concentration of various reagents will vary widely depending upon which protocols are employed, the nature of the analyte, the mip which is bound to the surface and the mip which is bound to the catalyst, the required sensitivity of the assay, and the like. In some instances, large excesses of one or the other of the mips may be employed, while in some protocols the sensitivity of the assay will be responsive to variations in the mip ratios.

In carrying out the calibrated assay of the present invention, it is necessary that both the measurement and calibration surfaces be contacted simultaneously with the sample and the signal producing system. It is also desirable that both surfaces be located close to one another, while they are immersed in the assay medium, to minimize any differences which might result from local variations in the medium. Conveniently, this may be accomplished by mounting both surfaces on a common rod or support. Mounting of the surfaces on a common support, however, is not required to practice the method of the present invention and it is necessary only that the surfaces be immersed in the various components of the signal producing system and sampled at the same time and for identical lengths of time. The surfaces may otherwise be handled independently without having an adverse effect on performance of the assay.

The common support for the surfaces is conveniently a rod or plastic film as used in the dip sticks of the prior art. The precise nature and dimensions of such dipsticks are not critical and may be chosen to conform with other components of the assay system, typically the sizes of the various reagent containers. It is desirable that both surfaces be placed at one end of an elongate dip stick so that they may be easily immersed in an relatively small sample, typically 100 $\mu$l to 2 ml. Mounting the surfaces adjacent each other also facilitates visual comparison of the surfaces to perform the final determination. The surfaces may be vertically or horizontally positioned.

As already indicated, more than two surfaces may be employed, involving either or both a plurality of measurement surfaces and a plurality of calibration surfaces. For example, a plurality of analytes may be simultaneously determined and/or a plurality of calibration surfaces provided to provide for a more quantitative result or a different calibration surface associated with each of the measurement surfaces for the different analytes.

A wide variety of protocols may be involved, where one or more solutions will be employed. Contact with the solutions may involve agitation or standing. Incubation steps may be involved, generally varying from about 0.5 min to 1 hr, more usually from about 2 min to 30 min.

The protocols will vary with the nature of the signal producing system as well as the analyte, and considerations of economy, efficiency and accuracy. The reagents of the signal producing system may be provided as separate solutions or may be dissolubly non-covalently bound to the surfaces, so as to diffuse into the sample solution.

Where the reagents of the signal producing system are provided separately, all of the reagents may be combined with the sample; or one or a plurality of sps members may be combined with the sample followed by a second solution with the remaining members of the signal producing system. For example, enzyme-labeled-mip may be combined with the sample solution, with the substrates and any coenzymes distributed between the sample solution and a second solution or all the remaining sps members added as a second solution, the second solution being referred to as the developer solution. Alternatively, the sps members may be non-covalently dissolubly bound to the surfaces, so as to rapidly dissolve into the sample solution upon contact with the sample solution.

Where a plurality of solutions are involved, the surfaces will be transferred from solution to solution. Usually, intermediate wash steps will not be required to remove adventitious non-specific binding.

The method and system of the subject invention may be used with any assay for an analyte employing a label producing a detectable signal. Competitive and non-competitive protocols may be employed: the analyte and the sps labeled analyte may compete for homologous mip on the measurement surface or they may successively bind or where the analyte has a plurality of binding sites, it may serve as a bridge between the mip bound to the measurement surface and the mip of the sps-labeled-mips. By varying the various mips on the surface and involved in the sps conjugate, as well as the number of solutions with which the surfaces are contacted and the members of the signal producing system, the protocols can be varied widely, depending upon the degree of quantitation desired, the sophistication of the user, and available equipment. Also, some or all of the same considerations will affect the nature of the calibration surface and the manner in which is the sps member is bound to the calibration surface.

The signal producing system may be non-catalytic or catalytic. The non-catalytic system will involve a plurality of signal producing labels, such as fluorescers or chemiluminescers, bound to a hub or particle, so that for a single binding event, a relatively large signal may result from a single binding event. Bound to the hub or particle will be a mip that will be chosen in accordance with the nature of the analyte. For an haptenic analyte, an antibody to hapten (antihapten) may be bound to the measurement surface. The measurement surface may then be immersed in the sample solution and the analyte will bind and fill a proportion of the binding sites. The particle-hapten conjugate may then bind to remaining available antihapten sites. Alternatively the particle-hapten conjugate may be combined with the sample solution and compete with the analyte for available binding sites on the measurement surface.

Catalytic systems may involve either the catalyst or the substrate bound to a mip. Where the substrate is bound to a mip, normally a hub will be employed with a plurality of substrates and one or more mips, much as in the non-catalytic system. Where one of the substrates is a coenzyme, the coenzyme may be recycled by using two enzyme systems, where the result is the production of a plurality of signal generating compounds due to the presence of a single coenzyme. These systems have been amply reported in the literature. Where the substrate is not cycled, the substrate will usually be a precursor to a fluorescer or result in chemiluminescence.

In cataltyic systems involving a single catalyst bound to a mip, usually an enzyme, the catalyst-bound-mip and analyte can be employed in a competitive mode, where the catalyst-bound-mip competes concurrently or consecutively for the homologous mip at the measurement surface. Thus, one could have the surfaces contact the sample containing the analyte either in combination with the catalyst-bound-mip or followed by contact with the catalyst-bound-mip. In the former case, the catalyst-bound-mip is in relatively limited amount and directly competes with the analyte for available mip binding sites on the measurement surface. In the latter case, the catalyst-bound-mip fills available binding sites which remain after binding of analyte to the measurement surface and, therefore, can be in greater excess of the analyte concentration of interest than in the former situation. After sufficient time for the mips to bind to the measurement surface, the surfaces may then be contacted with the appropriate substrates, including cofactors, which include a compound which results in a product which will bind to the surfaces and provide a detectable signal.

In another embodiment, a combination of catalysts, particularly having at least one enzyme, are employed, where one of the catalysts produces a product which is the substrate of the other catalyst. This is a preferred embodiment, particularly with two enzymes, in that it minimizes the number of reagent solutions required and/or washing requirements and provides for rapid production of the signal generating compound at the surfaces. In this embodiment, the measurement surface includes not only a mip, but also one of the two enzymes, preferably the first enzyme in the series. The enzyme-bound-mip is preferably the second enzyme in the series. The product of the first enzyme is an essential substrate for the second enzyme, so that the various substrates and cofactors necessary for the signal producing system may be combined with the second enzyme without concern as to premature reaction in an aqueous medium. Only upon combination with the surfaces will the substrate of the first enzyme be turned over to provide the product which is the substrate of the second enzyme.

Similar protocols may be employed as previously described, although the desirability of using a substrate solution separate from the solution containing the catalyst-labeled-mip is substantially diminished. The preferred protocol includes adding all of the members of the signal producing system to the sample; then introducing the surfaces to the resulting solution; allowing sufficient time for reaction to occur to provide for a change in a detectable signal at the surfaces; and then removing the surfaces and comparing the level of detectable signal at each of the surfaces as a measurement of the amount of analyte in the medium.

Alternatively, one could first contact the sample with the analyte, followed by the addition of the enzyme-bound-mip either concurrently with the substrates and cofactors or consecutively. As already indicated, an excess of the enzyme-bound-mip can be used in the competitive situation, where the analyte is first bound to its complementary mip on the surface. Where the analyte serves as a bridge, an excess of the enzyme-bound-mip may be used, regardless of whether the enzyme-bound-mip is added concurrently with or consecutively to the analyte, particularly where different monoclonal antibodies are used at the surface as compared to the enzyme-bound-mip. The concentration of substrates and cofactors will preferably be in substantial excess of their becoming a limiting factor in the turnover rate of the enzyme. That is, they will exceed the Michaelis constant for the enzyme.

The calibration surface will be varied depending upon the sensitivity desired and the number of factors to be paralleled between the calibration surface and the measurement surface.

The calibration surface will parallel the measurement surface in at least one binding event, preferably two, where the binding event involves the binding of homologous mips or enzyme-substrate (includes coenzyme). For non-catalytic signal producing systems, a mip will be bound to the calibration surface, different from the mip bound to the measurement surface. Desirably, the mip bound to the calibration surface will be of similar nature to the mip bound to the measurement surface, so that the two surfaces will have haptens, antigens or receptors, as appropriate.

For catalytic signal producing systems, the calibration surface need not involve a mip. The simplest catalytic calibration surface will be the catalyst bound to the surface, either covalently or non-covalently, where the catalytic activity will be provided at a predetermined value. Thus, during the assay measurement, the catalyst will be subject to the same extraneous factors and conditions on the calibration surface as the catalyst bound to the measurement surface. That is, temperature conditions, reagent stability, endogenous non-specific interference, as well as specific interference, localized fluctuations in conditions and concentrations, and the like, will all affect the production of the detectable product analogously at the two surfaces. Thus, the major sources of variation in generation of the signal generating compound will be affected in parallel ways on the measurement surface and the calibration surface.

The parallel relationship can be further enhanced by also providing for mip complex formation on the calibration surface. This can be achieved in a variety of ways. One way provides for a receptor for enzyme catalyst, which does not significantly affect the enzyme activity. Where the enzyme-bound-mip is in substantial excess over the amount which binds to the measurement surface in the analyte concentration range of interest, then the amount of enzyme which binds to the calibration surface will be substantially constant. However, the binding of the enzyme to its receptor, particularly antibody, will be affected in an analogous way to the binding of the analyte to its homologous mip.

One can bring the parallel closer by conjugating a mip to the catalyst different from the analyte bound to the catalyst. With a lig and analyte, one can have a different ligand bonded to the catalyst, where such different or second ligand may be bonded to the same catalyst molecule as the analyte or to a different catalyst molecule. Where the two ligands are bonded to the same catalyst, there will be a competition between the measurement surface and the calibration surface for the catalyst-bound-mip. Where the catalyst-bound-mip is in substantial excess, then the amount of catalyst-bound-mip which binds to the calibration surface will not be significantly affected by the concentration of analyte. In some instances, the catalyst-bound-mip may be in limited amount, that is, when it is not in substantial excess over the total available binding sites of both the measurement surface and calibration surface. Then the amount of catalyst which binds to the calibration surface will vary with analyte concentration. Otherwise, the sole variation in the amount of catalyst bound to the calibration surface will be as a result of fluctuations in conditions which affect the formation of mip complexes.

With the non-catalytic sps member or substrate label, one can also have two ligands (analyte and calibration ligand) bound to the hub or particle. Thus, depending on the concentration of the conjugate, a competitive or noncompetitive mode may be employed, where the two ligands are on the same or different conjugates and where, in the case of both ligands being on the same conjugate, the conjugate is present in limited amount or substantial excess. By substantial excess is intended that the concentration of the conjugate does not change significantly during the assay.

Normally, the calibration surface will provide a signal substantially independent of the amount of analyte in the assay medium. By appropriate choice of the component bound to the calibration surface, a detectable signal is provided which provides a predetermined concentration level. The detectable signal from the measurement surface will be approximately affected in the same manner as the production of the detectable signal at the measurement surface. The observed detectable signal at the calibration surface will, therefore, define a constant concentration level of analyte.

In determining the amount of analyte, one can compare the signal levels at the measurement and calibration surfaces and use the comparison as an indication of the presence of analyte above a predetermined level. Alternatively, one can obtain a semi-quantitative or quantitative determination by dividing the signal level at the measurement surface by the signal level on the calibration surface. In this way non-specific effects of the assay medium on signal production will be substantially divided out.

Where the mip in the sps member-bound-mip is a receptor, one has the additional opportunity to provide for receptor on the calibration surface which binds to an antigenic site on the receptor portion of the sps member-bound-receptor. Where the receptor on the surface is an antibody, one can have an anti(antibody), which may bind to a convenient determinant site of the antibody. In this manner, the mip of the sps member-bound-mip can act as a receptor in binding to the complementary mip bound to the measurement surface and as a ligand in binding to its complementary mip bound to the calibration surface.

In most cases, it will be desirable that the user of the subject apparatus make as few measurements and as few transfers as possible. That is, the manufacturing process will provide most, if not all, with the exception of the measurement of the sample, measurements of reagents. Secondly, it is desirable that as few transfers as possible be involved in the protocol, not only to enhance efficiency and reduce the introduction of error, but also to reduce the total time for the test.

In the simplest protocol, one would have all the reagents incorporated on the surfaces or combined in an appropriate formulation, conveniently a lyophilized powder formulation.

Where the reagents are incorporated on the surface, for example, by impregnation, encapsulation, adhesion by means of a water soluble adhesive, etc., the apparatus need only be placed in the sample solution. The measurement and calibration surfaces will be subject to the same effects, so long as the rate of solution is very rapid.

The lyophilized powder formulation would be dissolved in a measured amount of an aqueous medium containing the sample. After a sufficient time for the solution to become homogeneous, the surfaces may be introduced into the sample solution. For non-catalytic signal producing systems, by appropriate choice of mips, only a single dip of the surfaces would be required. With catalytic systems, a single formulation could be used where the signal producing system involves two enzymes, related by one enzyme producing a product which is the substrate of the other enzyme. By having the first enzyme bound to both the measuring surface and the calibration surface, one can combine the second enzyme with the substrate for the first enzyme without concern about premature reaction, since until the first enzyme produces the necessary substrate for the second enzyme, there will be no reaction.

Where only a single catalyst is employed in the signal producing system, either one will have at least two solutions with separate contacting of the surfaces with the two solutions, one of the solutions having the substrate for the catalyst and the other solution having the catalyst-bound-mip; or catalyst-bound-mip may be bound dissolubly to the surface and a single substrate containing reagent solution employed.

The signal generating compound may provide an increase or decrease in the observed signal. When generated by a catalyst, the signal generating compound will preferentially bind to the surfaces and provide a detectable signal, which may be visually detected, or detected by a reflectometer or fluorometer. The signal generating compound will normally be substantially insoluble in the medium in which it is produced and will be derived either directly or indirectly from a catalytic product. By having the signal generating compound produced adjacent to the surfaces by the presence of catalyst bound to the surfaces, the proportion of the total signal generating compound resulting from binding of the signal generating compound to the surfaces from the bulk solution will be minimized.

In a number of situations, a scavenger may be desirable. For example, where the two enzymes are used in the signal producing system, by having a scavenger in the bulk solution for the product of the first enzyme, production of the signal generating compound in the bulk medium can be further reduced. Also, where the signal generating compound is produced in the presence of unbound enzyme-bound-mip in the bulk medium, a scavenger for the signal generating compound in the bulk medium may be useful. Alternatively, an enzyme inhibitor may be employed, which selectively deactivates the enzyme in solution but is substantially inactive toward the enzyme bound to the surface. This can be achieved by employing reversible inhibitors or suicide inhibitors bound to a large porous particle which inhibits access of the inhibitor bound to the particle to the binding site of the enzyme bound to the surface.

For the most part, the signal generating compound will enhance the signal at the surface. However, there is also the possibility for reducing the signal at the surface. For example, where the surface is fluorescent, one can provide for production of quencher which will diminish the surface fluorescence. Alternatively, one could have the surface colored with one dye, where the observed coloration would change upon precipitation of a different dye upon the surface. Alternatively, one could employ a combination of enzymes, where the first enzyme produces a signal generating compound and the second enzyme destroys the signal generating compound, or an essential intermediate is destroyed. For example, by having glucose oxidase and horse radish peroxidase on the surface, with catalase bound to a mip, the more catalase which binds to the surface, the less dye that would be produced. Thus, by having a third enzyme present as the enzyme-bound-mip, the amount of enzyme-bound-mip which binds to a surface would be related to the decrease in the observed production of the signal generating compound.

For quantitation, one can develop a ratio of signal level on the measurement surface as related to the signal level on the calibration surface. Thus, by providing for a particular time period from the initiation of production of a signal generating compound to termination of further production of the signal generating compound, the ratio of the signal from the measurement surface and calibration surface can be related to standard values for quantitating the amount of analyte. Where the signal producing compound is produced at a constant rate, the time is not a critical factor, so long as a sufficient change in signal occurs at both the measurement surface and calibration surface, but not so long that a change in signal can no longer be observed at the surfaces. Thus, the ratio will provide a result which is relatively insensitive to time, temperature and endogenous interference. Alternatively where two calibration surfaces are employed, the ratio of the signals at these surfaces can be used in lieu of a time measurement.

The following are two exemplary protocols employing a single enzyme and a combination of enzymes. The analyte is a ligand and the two surfaces have receptors for different ligands, the second ligand being referred to as the calibration ligand. The enzyme is conjugated with both the analyte analog and the calibration ligand. A sample is obtained and dissolved in an aqueous buffered medium to a predetermined volume. A lyophilized mixture containing the enzyme-bound-diligand (analyte and calibration ligand) stabilizers, excipients, and, optionally, buffer, is added to the sample to provide a solution containing the analyte and the enzyme-bound-diligand in sufficient amount to compete with the analyte for the receptor at the measurement surface, while still being available to bind to a limited degree to the calibration surface. The two surfaces are simultaneously introduced into the solution and allowed to stand for a reasonable time, whereby the analyte binds to the measurement surface and the enzyme-bound-diligand is distributed between the measurement surface and the calibration surface in relation to the amount of analyte in the assay medium.

After a sufficient time for binding, generally from about 1 to 10 minutes, the two surfaces are separated from the assay medium and introduced into a development solution. After a reasonable period for sufficient signal generating compound to be formed on the surfaces, the surfaces are removed, and the signals on the two surfaces visually compared. By appropriate choice of the amount of mip on the calibration surface, if the signal from the calibration surface is greater, for example darker, than the signal from the measurement surface, this would indicate that the analyte was present in less than a predetermined amount. By measuring the signal from the two surfaces, and determining the ratio, the ratio could be compared to standards which would then indicate the actual amount of analyte present. Thus, one can obtain an immediate qualitative result by visual observation and if one wishes a quantitative result, by careful measuring of the signal at the two surfaces, and comparison to standards, a quantitative result can be obtained.

In the next protocol, a combination of enzymes will be used which will allow for a single formulation and a single contacting of the sample and reagent solution with the surfaces for production of the signal generating compound. For comparative purposes with the prior protocol, in this case, two (enzyme-bound-ligand)s will be employed, using the same enzyme but two different haptens, one hapten being the analyte and the other hapten referred to as the calibration hapten. The measurement surface will have antibody to the analyte hapten, while the calibration surface will have antibody to the calibration hapten. While the two haptens should not be cross-reacting, they should be desirably similar in their properties, so that the formation of the respective binding complexes should be affected analogously by fluctuations in conditions and endogenous materials. The receptor on the calibration surface is present in a predetermined amount to provide for production of signal generating compound independent of the amount of analyte in the assay medium. In addition to the receptors, the surfaces will also have comparable amounts of a first enzyme which produces a product which is a substrate for the enzyme of the enzyme-bound-ligand.

In the exemplary protocol, the two enzyme-bound-ligands do not compete for receptors on the respective measurement and calibration surfaces. Therefore, the amount of enzyme-bound-calibration ligand which binds to the calibration surface will not be a function of the amount of analyte in the medium. Since the (enzyme-bound-ligand)s will not react with the substrates provided for the assay medium, in the absence of the product of the enzyme bound to the surfaces, all of the reagents may be combined in a single formulation which may then be combined with the sample. The enzyme-bound-ligand which competes with the analyte for the mip on the measurement surface will be in limited amount, so as to allow for variation in the amount of enzyme-bound-ligand which binds to the measurement surface in relation to varying amounts of analyte present in the medium. As previously indicated, the formulation may include buffers, stabilizers, excipients, and the like, in addition to the (enzyme-bound-ligand)s and substrates.

The formulation may be first dissolved in an aqueous medium to provide a solution having the reagents at the appropriate concentrations. An aliquot of the solution may be taken of a predetermined volume and a sample measured into the solution. Since the first enzyme is essential for the enzymatic reaction to proceed, the surfaces are then introduced into the solution and a sufficient time allowed for the signal generating compound to form at the surfaces, at which time the surfaces are removed and the surfaces either visually inspected or the level of signal generation determined by an appropriate apparatus.

Since the signal level of the calibration surface is independent of the analyte concentration, one can provide that for a signal level at the measurement surface smaller than the signal level at the calibration surface, the analyte will be present in greater than a predetermined amount. Alternatively, by employing ratios of the signal levels of the measurement surface and calibrator surface and comparing these to standards prepared employing known amounts of analyte, one can quantitate the amount of analyte present in the sample.

For a description of various techniques which find application in the subject invention, see U.S. Pat. No. 4,299,916, Cols. 7–16, which subject matter is incorporated herein by reference.

A further alternative embodiment, which ordinarily will not be preferred, is to employ a combination of enzymes, where each is bound to a mip and each binds to the measurement surface in proportion to the amount of analyte present in the assay medium. One could then provide for the same combination of enzymes to be bound to the calibration surface, either initially or through the intermediacy of mip complex binding, where the mip may provide a receptor for each of the two enzymes or by having a common ligand bound to the two enzymes, where the enzyme molecules may be the same or different enzyme molecules to which the analyte is bound.

MATERIALS

The components employed in the subject assay will be the analyte, the measurement and calibration surfaces, the signal producing system and, as appropriate, poly(ligand analog) or polyvalent receptor. The signal producing system will include at least one catalyst-bound-mip and a solute which is a substrate for the catalyst. Frequently, the signal producing system will have additional members.

Analyte

The ligand analytes of the present invention are characterized by being monoepitopic or polyepitopic. The polyepitopic ligand analytes will normally be poly(amino acids), i.e., polypeptides and proteins, polysaccharides, nucleic acids, and combinations thereof. Such combinations include bacteria, viruses, chromosomes, genes, mitochondria, nuclei, cell membranes and the like.

The precise nature of the analytes together with numerous examples thereof are disclosed in U.S. Pat. No. 4,299,916 to Litman, et al., particularly columns 16 to 23, the disclosure of which is incorporated herein by reference.

Measurement and Calibration Surfaces

The underlying surface provided for the immobilization of mip and/or catalyst to form the measurement surface and calibration surface can vary widely. Generally, the underlying structure will be the same for both the surfaces, being chosen so as not to be strongly adsorbent for members of the signal producing system to minimize interference with the assay. The underlying structures of the surfaces may take different forms, have different compositions and may be a mixture of compositions or laminates or combinations thereof. The material chosen for the surfaces must be able to interact with the signal generating compound by desolubilization of the signal generating compound or complexation reaction or interaction of another compound bonded to the surface, so as to form, destroy or interact with the signal generating compound.

The surfaces may assume a variety of shapes and forms and may have varied dimensions, depending on the manner of use and measurement. Illustrative surfaces may be pads, discs, or strips which may be flat, concave or convex. The thickness is not critical, generally being from about 0.1 to 2 mm thick and of any convenient diameter or other dimensions. Typically the surfaces will be supported on a common member, such as a rod, tube, capillary, fiber, strip, disc, plate, cuvette and the like, although the present invention contemplates supporting each surface on a separate mechanical support. The surfaces may form an integral part of the support or be distinct from the support, typically forming an applied layer on the support or spaced apart from the support and supported by two or more spacers.

The surfaces will typically be porous, with various pore sizes employed, depending on the nature of the system. The surfaces may be polyfunctional or be capable of being polyfunctionalized, so as to permit covalent bonding of mips, as well as to permit bonding of other compounds which form a part of the signal producing system. The precise nature of the surfaces is discussed in detail in U.S. Pat. No. 4,299,916 to Litman, et al., incorporated herein by reference.

Binding of mips to the surface material to form the measurement and calibration surfaces may be by well known techniques, commonly available in the literature. See, for example, "Immobilized Enzymes," Ichiro Chibata, Halsted Press, New York (1978) and Cuatrecasas, *J. Biol. Chem.*, 245:3059 (1970).

A wide variety of organic and inorganic polymers, both natural and synthetic, and combinations thereof, may be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), silicones, polyformaldehyde, cellulose, cellulose acetate, nitrocellulose, etc. Other materials which may be employed include paper, glasses, ceramics, metals, metaloids, semiconductive materials, cermets, silicates or the like. In addition are included substances that form gels, such as proteins, e.g., gelatins, lipopolysaccharides, silicates, agarose; and polyacrylamides or polymers which form several aqueous phases, such as dextrans, polyalkylene glycols (alkylene of 2 to 3 carbon atoms) or surfactants, e.g., amphiphilic compounds, such as phospholipids, long chain (12–24 carbon atoms) alkyl ammonium salts and the like.

Signal Producing System

The signal producing system may be non-catalytic or catalytic, in each instance providing amplification of the signal level for each mip binding event.

In the non-catalytic system, the amplification is as a result of having a plurality of signal generating functionalities bound to a hub or particle. When the hub or particle binds to the surface through mip binding, a large number of the signal generating functionalities also become bound. Thus, there is a fixed ratio of amplification.

The common functionalities that are employed are fluorescers and chemiluminescers, or precursors thereof. Descriptions of exemplary compounds may be found in the U.S. Patent cited previously.

The hub or particle can be any convenient organic or inorganic nucleus, such as latex particles, glasses, etc. These have also be extensively described in the literature. The size of the particle will generally vary from about 10 to 100$\mu$ in diameter.

The catalytic signal producing system provides for the production of a compound, which is normally the signal generating compound, but in some instances may react with another compound bound to the surfaces with the production, enhancement or destruction of the signal generating compound. While both enzymatic and non-enzymatic catalysts may be employed, usually there will be at least one enzyme catalyst employed in the catalytic signal producing system. In the event of there being only one catalyst, this catalyst will be conjugated to a mip for binding to the measurement surface through complex formation. In addition to the catalyst, there must be a solute which undergoes a transformation which results in a change in a detectable signal at the measurement surface.

For the most part, the product resulting from the transformation catalyzed by the catalyst-bound-mip will be the signal generating compound. Therefore, where there is only one catalyst, usually an enzyme, the signal producing system will involve the catalyst-bound-mip and its substrate. In some instances it may be desirable to have a "coupler" bound to the surface, where the catalytic product reacts with the "coupler" compound to produce the signal generating compound.

Preferably, two catalysts will be employed, either a combination of an enzyme and a non-enzyme catalyst or two enzymes, where the two catalysts are related in that the product of one is the substrate of the other. In this system, there need be only one solute or substrate which can undergo successive changes catalyzed by the catalysts, which results in the compound involved with production of a detectable signal. For the most part, however, there will normally be a substrate for the first enzyme in the series and a second compound, which serves as a precursor to the compound involved in the production of the signal, normally providing the compound which produces the signal. Thus, the product of the first enzyme may react with the precursor to the signal producing compound to provide the signal generating compound.

For the most part, the involved reactions will be hydrolysis or redox reactions. In the case of hydrolysis, substitution of a dye by a water solubilizing compound joined by an enzymatically labile bond, where two enzymatic steps are required to result in the insoluble dye product is illustrative of this type of system. By contrast, in redox reactions, the first enzyme can produce an essential substrate for the second enzyme, where the second enzyme catalyzes the reaction between the product of the first enzyme and the dye precursor.

The enzymatic reaction may involve modifying the solute to a product which is the substrate of another enzyme or production of a compound which does not include a substantial portion of the solute, which serves as an enzyme substrate. The first situation may be illustrated by glucose-6-phosphate being catalytically hydrolyzed by alkaline phosphatase to glucose, where glucose is a substrate for glucose oxidase. The second situation may be illustrated by glucose being oxidized by glucose oxidase to provide hydrogen peroxide which would enzymatically react with the signal generator precursor to produce the signal generator.

Coupled catalysts can also involve an enzyme with a non-enzymatic catalyst. The enzyme can produce a reactant which undergoes a reaction catalyzed by the non-enzymatic catalyst or the non-enzymatic catalyst may produce a substrate (includes coenzymes) for the enzyme. For example, Meldola blue could catalyze the conversion of NAD and hydroquinones to NADH which reacts with FMN oxidoreductase and bacterial luciferase in the presence of long chain aldehydes to product light. A wide variety of nonenzymatic catalysts which may be employed in this invention are found in U.S. Pat. No. 4,160,645, issued July 10, 1979, the appropriate portions of which are incorporated herein by reference. The nonenzymatic catalysts employ as reactants a first compound which reacts by a 1-electron transfer and a second compound which reacts by a 2-electron transfer, where the two reactants are capable of reacting with each other slowly, if at all, in the absence of the catalyst.

Various combinations of enzymes may be employed to provide a signal generating compound at the surface. Particularly, combinations of hydrolases may be employed to produce an insoluble signal generator. Alternatively, combinations of hydrolases and oxidoreductases can provide the signal generating compound. Also, combinations of oxidoreductases may be used to produce an insoluble signal generating compound. The following table is illustrative of various combinations which may be employed to provide for preferential production of the signal generating compound at the surface. Usually there will be a preferred catalyst at the surface, since as indicated previously, by appropriate choice of the catalyst at the surface, a greater number of reagents may be combined in a single formulation.

In the following table the first enzyme is intended to be bound to the surface and the second enzyme to a mip, although in particular situations it may be desirable to reverse their positions.

TABLE 1

INTERRELATED TWO ENZYME SYSTEMS

| First Enzyme | Second Enzyme | Solute | Signal Generation | Reactions |
|---|---|---|---|---|
| 1. Galactose oxidase | horse radish peroxidase | $\beta$-D-galactose | 4-Cl—1-naphthol dye | 1. galactose + $O_2 \rightarrow$ D-galactono-$\delta$-lactone + $H_2O_2$<br>2. $H_2O_2$ + 4-Cl—1-naphthol $\rightarrow$ dye |
| 2. uricase | horse radish peroxidase | urate | o-dianisidine dye | 1. urate + $O_2 \rightarrow$ allantoin + $H_2O_2$<br>2. $H_2O_2$ + o-dianisidine $\rightarrow$ dye |
| 3. glucose oxidase | microperoxidase | $\beta$-D-glucose | bis-toluidine dye | 1. glucose + $O_2 \rightarrow$ D-glucono-$\delta$-lactone + $H_2O_2$<br>2. $H_2O_2$ + bis-toluidine $\rightarrow$ dye |
| 4. esterase | $\beta$-glucuronidase | 2,2-bis(3'-chloro-4'-glucuronyloxyphenyl)-phthalide choline chloride ester | 3',3''-dichlorophenolphthalein | 1. 2,2-bis(3'-chloro-4'-glucuronyloxyphenyl) phthalide choline chloride $\rightarrow$ 2,2-bis (3'-chloro-4'-glucuronyloxyphenyl)-phthalide<br>2. 2,2-bis(3'-chloro-4'-glucuronyloxyphenyl)phthalide $\rightarrow$ 3',3''-dichlorophenolphthalein |
| 5. alkaline phosphatase | peroxidase | 4-Cl—1-naphthyl phosphate | 4-Cl—1-naphthol dye | 1. 4-Cl—1-naphthyl phosphate $\rightarrow$ 4-Cl—1-naphthol<br>2. 4-Cl—1-naphthol $\rightarrow$ dye |
| 6. hexokinase | glucose-6-phosphate dehydrogenase | glucose | iodonitrotriphenyl formazan | 1. glucose + ATP $\rightarrow$ glucose-6-phosphate<br>2. glucose-6-phosphate + NADP $\rightarrow$ NADPH phenazine methosulfate + NADPH + triphenyltetrazolium chloride $\rightarrow$ formazan |
| 7. akaline phosphatase | $\beta$-galactosidase | $O^7$—($\beta$-D-galactosidyl-6'-phosphate) 4-alkylumbelliferone | 4-alkylumbelliferone | 1. $O^7$—($\beta$-D-galactosidyl-6'-phosphate) 4-alkylumbelliferone $\rightarrow$ $O^7$—($\beta$-D-galactosidyl) 4-alkylumbelliferone<br>2. $O^7$—($\beta$-D-galactosidyl) 4-alkylumbelliferone $\rightarrow$ 4-alkylumbelliferone |

Quite obviously, many of the dyes indicated above may be substituted with other dyes which have the proper solubility requirements or which can be modified to have the proper solubility requirements for the subject invention. In addition, it should be appreciated, that by having a high localized concentration of the dye, the dye will rapidly bind to the surface. In addition, any incremental amount of dye which diffuses from the bulk solution to the surface will not significantly affect the amount of dye which precipitates on the surface. Depending upon the nature of the dye, either light absorption by the dye or, if fluorescent, light emission may be measured.

Instead of a chemical reaction to an enzyme product to produce the signal generating compound, the environment of the enzyme product can be selectively modified, upon binding to the surface, so as to produce the signal generating compound. For example, one could hydrolyze an ester or ether to produce an insoluble colorless form of a charge sensitive dye at the surface. The local charge at the surface will be made substantially different from the bulk solution by having charged groups on the surface. By employing a signal generating compound which is sensitive to proton concentration, the observed signal from the product bound to the surface would differ greatly from the product in the bulk solution or liquid phase. Fluorescer quencher pairs may also be employed where the solute produces an insoluble quenching product.

Ancillary Materials

Various ancillary materials will frequently be employed in the subject assays. Particularly, enzyme substrates, cofactors, activators, scavengers, inhibitors or the like may be included in the assay medium.

In addition, buffers will normally be present, as well as stabilizers. Frequently in addition to these additives, additional proteins may be included, such as albumins; or surfactants, particularly non-ionic surfactants, e.g., polyalkylene glycols, or the like.

EXPERIMENTAL RESULTS

The following examples are offered by way of illustration and not by way of limitation.

All percents and parts not otherwise indicated are by weight, except for mixtures of liquids which are by volume. When the solvent is not indicated, water is intended. All temperatures not otherwise indicated are centigrade. The following abbreviations are employed: CMM—$O^3$—carboxymethyl morphine; HRP—horse radish peroxidase; NHS—N-hydroxy succinimide; EDCI—N-ethyl N'-(3-dimethylaminopropyl) carbodiimide; DMF—N,N-dimethyl formamide; THF—tetrahydrofuran; BSA—bovine serum albumin; GO-AMINE—glucose oxidase-amine; Triton QS 44—anionic surfactant (Rohm and Haas Co.); NaAZ—Sodium azide; MOPS—3-N-morpholinopropanesulfonic acid (Calbiochem); CDI—1,1'-Carbonyl diimidazole.

EXAMPLE 1

Preparation of Anti-Morphine Paper

The following experiments employed antimorphine coupled to a paper support prepared in bulk as follows. Whatman 1C Paper (16 ft × 10.63 in) was rolled on a one-inch diameter spool with two screens separating adjacent layers of paper to allow penetration by reagents. The resulting cartridge was inserted into a reactor where it was freeze dried under vacuum over night. CDI (85 gm Polysciences, Lot Number 12087, Catalog No. 15750) was dissolved in 2.5 L of dichloromethane. The solution was recirculated through the reactor with a centrifugal pump at a flow rate of approximately 4 L/min. for two hours. The paper was then washed three times with dichloromethane (2.5 L) and dried with nitrogen (approximately 7 L/min) for three hours and stored at room temperature overnight.

A mixture of antibody to morphine (0.2 mg/ml) and GO-AMINE (0.1 mg/ml) in phosphate buffer (2.8 L) at 24° C. was recirculated through the reactor at approximately 2 L/min for four hours. The paper was then washed four times with phosphate buffer (4 L) and stabilized with 2.5 L of a solution containing sucrose (15%) and BSA (2 mg/ml). Excess fluid was removed with nitrogen (40 psi for 1 min, 80 psi for 15 sec). The paper was then vacuum dried with nitrogen bleeding (250 ml/min) for 89.5 hr.

EXAMPLE 2

Preparation of Anti-HRP Paper

Two rolls of filter paper were prepared with HRP as follows:

A first roll of Whatman 1C Paper (12 ft × 10.63 in) was rolled on a two-inch diameter spool with a pair of wire screens separating adjacent layers. A second roll of Whatman 1C paper (16 ft × 10.63 in) was rolled on a one-inch diameter spool, also with adjacent layers separated by a pair of wire screens. The first roll was placed in a first reactor and the second roll was placed in a second reactor, where both rolls were dried under vacuum over night with nitrogen bleeding to remove moisture.

CDI (170 gm) was dissolved in 5.0 L of dichloromethane, which was recirculated at 4 L/min through the reactors connected in series. The papers were then washed three times with 4.5 L of dichloromethane, and then dried for three hours with nitrogen (6 L/min) and overnight at 200 ml/min.

Paper from the second reactor was treated with a mixture of antibody to HRP (29.56 μg/ml), non-immune sheep IgG (220 μg/ml) and QS44 (2%, W/V) in phosphate buffer adjusted to pH6.94 with 1.0 M NaOH. The mixture was incubated overnight with stirring. GO-Amine (500 mg) (see below for preparation) with NaAZ was added to the solution, the final volume equal to 2.5 L. Final concentration of GO-amine was 0.2 mg/ml.

The solution was recirculated through the second reactor (2 L/min) for five hours. The reactor was then washed four times with phosphate buffer (4 L) and stabilized with 2.5 L of sucrose (15%) and BSA (2 mg/ml). Excess fluid was removed under pressure and the paper dried under vacuum with nitrogen bleeding (2.5 L/min).

Glucose oxidase (Sigma, E.C. 1.1.3.4) was concentrated from 360 ml to 60 ml with Amicon PM10 membrane at a pressure below 30 psi. The concentrate of glucose oxidase was dialyzed twice against 4 L of water at 4°, filtered and shown spectrophotometrically to have a concentration of 32 mg/ml. To 51.5 ml of the glucose oxidase solution was added dropwise 5.15 ml of 0.2 M sodium periodate, the reaction occurring over 25 min. The product was chromatographed on a 2.5 × 60 cm column of Sephadex G-50 using 2 mM sodium acetate pH 4.5, and the major glucose oxidase peaks pooled to yield 91.5 ml of a solution containing the aldehyde derivative. To the solution was added dropwise 6 ml of 3 M ethylene diamine in 0.2 M sodium carbonate, pH 9.5, and the reaction allowed to proceed for 3 hr. To the mix was then added about 3.9 ml of 10 mg/ml sodium borohydride, the mixture incubated overnight and then chromatographed to remove the sodium borohydride.

EXAMPLE 3

Conjugation of Morphine to HRP

Into a reaction flask were combined CMM (35.9 mg), NHS (12.65 mg) and EDCI (21.12 mg) in DMF (1.1 ml). The mixture was then flushed with nitrogen and stirred overnight at room temperature to form the activated ester of CMM. To a mixture of HRP oxyamine (1.9 mg/ml) (see below for preparation) in 21 ml of carbonate buffer (pH 9.5) was added the activated ester in 10 μl increments over a period of 1.5 hours to a molar ratio end point of 50:1 CMM:HRP, while maintaining the reaction mixture at 4° C. The reaction mixture was then applied to a 2×30 cm column of G50 Sephadex and eluted with 0.1 M phosphate, 0.2 M NaCl, pH 7.0 buffer and the protein monitored. The protein fractions were pooled.

To 5 ml of 10 mg/ml HRP in 5 mM sodium acetate, pH 4.5 buffer, was added 50 ml 0.2 M sodium iodate and the mixture stirred for 30 min, followed by chromatography on a G-50 Sephadex column, eluting with 2 mM sodium acetate buffer, pH 4.5. The protein fractions were pooled to 29 ml, the mixture cooled to 4° and 2.9 ml of 0.2 M 2,2'-oxy-bis-ethylamine in 0.5 M carbonate buffer, pH 9.5 at 4° added. The pH of the mixture was adjusted to 9.5 with 1 N sodium borohydride-water solution added and the mixture allowed to react for 3.5 hr, followed by chromatography through a Sephadex G-50 column.

The above procedure was repeated using 400 mg of HRP and 3.5 g of 2,2'-oxy-bis-ethylamine. No significant change in enzyme activity was observed between the native amine and the modified amine, which had about four additional amino groups.

EXAMPLE 4

Preparation of Dipsticks

For use in assays, ¼ in. discs were punched in the anti-morphine paper of Example 1 and the anti-HRP paper of Example 2. The discs were then attached side-by-side to one end of a plastic stick to form the dipstick.

EXAMPLE 5

Standard Curve as a Function of Morphine Concentration

Standard solutions of 0.1 M phosphate buffer, 0.2 M NaCl (2 ml, pH 7.0) were spiked with 0, 100, 330 and 1,000 ng/ml morphine in duplicate. Dipsticks prepared as in Example 4 were immersed in each solution for one min at room temperature. Without washing, the dip sticks were each placed in 2 ml of a developer solution, shaken for 5 sec and allowed to incubate for 9 min. The developer included glucose MOPS (50 mM, pH 6.8), BSA (2 mg/ml), 4-Cl-1-naphthol (0.2 mg/ml) and the HRP-Morphine conjugate prepared in Example 3 (200 ng/ml). After incubating for 9 min, the dipsticks were removed, the paper discs blotted and read on a MacBeth Series 1,500 reflectance spectrophotometer. The results are given in Table 1, where $R_C$ refers to the reflectance of the calibrator disc and $R_M$ refers to the reflectance of the morphine disc. $R_C$ and $R_M$ are represented in color difference units which are provided by the Macbeth reflectance spectrophotometer.

TABLE 1

| [Morph.] | $R_C$ | Avg.* | $R_M$ | Avg. | $R_C - R_M$ | $R_M/R_C$ |
|---|---|---|---|---|---|---|
| 0 | 23.66; 22.5 | | 18.07; 18.69 | 18.4 | 4.4 | 0.744 |
| 100 ng/ml | 22.43; 22.93 | | 14.07; 14.47 | 14.8 | 8.0 | 0.53 |
| 330 ng/ml | 22.43; 22.24 | | 14.13; 13.75 | 13.9 | 8.9 | 0.48 |
| 1000 ng/ml | 24.14; 22.22 | | 12.75; 11.85 | 12.3 | 10.5 | 0.38 |
| | | 22.8 ± 0.71 | | | | |

*Average of all $R_C$.

The results indicate that the reflectance displayed by the calibrator disc is independent of morphine concentration in the test sample, while the reflectance of the morphine disc decreases as the concentration of morphine increases. By employing the ratio of the two values from the measurement and calibrator discs, a standard curve is established for the quantitation of morphine.

EXAMPLE 6

Standard Curve as a Function of Morphine Concentration and Development Time

Standard solutions of morphine and phosphate buffer were prepared as in Example 5, except that eight replicates were prepared at each concentration for a total of 40 samples. Dip sticks were incubated in each of the test samples for one minute and thereafter placed in developer solution (Example 5) for the times indicated. The results are summarized in Table 2.

TABLE 2

| [Morph.] | Development time | $R_C$ | Avg* | $R_M$ | Avg | $R_M/R_C$ |
|---|---|---|---|---|---|---|
| 0 | 5 | 14.1; 11.9 | — | 9.5; 9.2 | 9.4 | 0.79 |
| | 7 | 14.7; 15.7 | — | 12.0; 12.3 | 12.7 | 0.78 |
| | 10 | 17.8; 20.7 | — | 15.4; 15.5 | 15.5 | 0.77 |
| | 15 | 24.3; 24.8 | — | 21.5; 20.9 | 21.2 | 0.84 |
| 10 | 5 | 14.9; 13.7 | — | 7.7; 7.6 | 7.6 | 0.64 |
| | 7 | 16.4; 16.9 | — | 10.0; 10.7 | 10.3 | 0.64 |
| | 10 | 20.1; 20.0 | — | 13.2; 15.2 | 14.2 | 0.71 |
| | 15 | 25.5; 25.0 | — | 18.0; 19.3 | 18.6 | 0.74 |
| 30 | 5 | 9.9; 11.7 | — | 5.1; 6.8 | 6.0 | 0.51 |
| | 7 | 16.7; 16.9 | — | 9.3; 9.4 | 9.4 | 0.58 |
| | 10 | 21.0; 20.7 | — | 9.9; 12.1 | 11.0 | 0.55 |
| | 15 | 24.1; 25.4 | — | 15.0; 14.7 | 14.9 | 0.60 |
| 100 | 5 | 11.2; 10.9 | — | 5.2; 5.5 | 5.4 | 0.46 |
| | 7 | 16.9; 16.1 | — | 7.8; 7.8 | 7.8 | 0.48 |
| | 10 | 18.1; 19.9 | — | 11.3; 10.9 | 11.1 | 0.56 |
| | 15 | 24.7; 26.3 | — | 12.7; 12.8 | 12.8 | 0.51 |
| 300 | 5 | 11.6; 11.1 | 11.8 | 5.2; 5.6 | 5.4 | 0.46 |
| | 7 | 14.8; 14.8 | 16.1 | 6.9; 6.9 | 6.9 | 0.43 |
| | 10 | 19.4; 20.7 | 19.9 | 9.3; 9.3 | 9.3 | 0.47 |
| | 15 | 24.5; 25.2 | 25.0 | 11.9; 10.0 | 10.9 | 0.44 |

*Average of all $R_C$ at each time.

EXAMPLE 7

Reproducibility

Sixteen samples of urine, each from a different donor, were each divided into four portions of 2 ml. Two portions of each sample were then spiked with morphine to a final concentration of 300 ng/ml. Dip sticks (Example 4) were placed in each portion and incubated for one minute. The dip sticks were removed and placed in developer solution (2 ml) prepared as in Example 5. Each dip stick was developed for nine minutes and the results are shown in Table 3.

TABLE 3

| SAMPLE | MORPHINE | $R_C$ | $R_M$ | $R_M/R_C$ |
|---|---|---|---|---|
| 1 | NO | 14.71 | 19.43 | 1.32 |
|   | YES | 15.3 | 12.5 | 0.83 |
| 2 | NO | 13.9 | 17.5 | 1.26 |
|   | YES | 14.7 | 11.6 | 0.79 |
| 3 | NO | 15.3 | 17.9 | 1.17 |
|   | YES | 13.9 | 12.3 | 0.88 |
| 4 | NO | 14.7 | 18.1 | 1.24 |
|   | YES | 16.0 | 13.2 | 0.83 |
| 5 | NO | 14.0 | 16.8 | 1.20 |
|   | YES | 15.4 | 11.1 | 0.72 |
| 6 | NO | 12.0 | 17.2 | 1.43 |
|   | YES | 12.9 | 9.8 | 0.76 |
| 7 | NO | 13.1 | 16.1 | 1.23 |
|   | YES | 14.2 | 13.4 | 0.94 |
| 8 | NO | 13.0 | 16.7 | 1.29 |
|   | YES | 13.6 | 11.4 | 0.84 |
| 9 | NO | 16.3 | 19.12 | 1.18 |
|   | YES | 15.9 | 13.8 | 0.87 |
| 10 | NO | 14.3 | 18.4 | 1.28 |
|   | YES | 15.3 | 12.8 | 0.83 |
| 11 | NO | 14.7 | 18.1 | 1.24 |
|   | YES | 15.2 | 12.1 | 0.79 |
| 12 | NO | 13.7 | 17.4 | 1.27 |
|   | YES | 13.2 | 12.1 | 0.91 |
| 13 | NO | 12.7 | 17.7 | 1.40 |
|   | YES | 12.7 | 11.5 | 0.90 |
| 14 | NO | 15.7 | 19.2 | 1.23 |
|   | YES | 16.6 | 13.1 | 0.79 |
| 15 | NO | 13.3 | 17.9 | 1.35 |
|   | YES | 12.6 | 10.0 | 0.79 |
| 16 | NO | 14.2 | 18.6 | 1.31 |
|   | YES | 14.2 | 11.8 | 0.83 |

EXAMPLE 8

Effect of Varying the Concentration of HRP-Morphine Conjugate In the Developer Solution Two developer solutions were prepared as in Example 5, except that the first solution included a HRP-Morphine conjugate, concentration at 150 ng/ml, and the second solution of 300 ng/ml.

The results are shown in Table 4.

TABLE 4

| [Morph.] | [HRP-Morph] | Development time | $R_C$ | $R_M$ | $R_M/R_C$ |
|---|---|---|---|---|---|
| 0 | 150 | 18 | 18.56; 17.82; 17.08 | 12.92; 12.31; 12.60 | 0.71 |
|   | 300 | 9 | 16.17; 13.80; 15.26 | 10.31; 9.89; 11.06 | 0.69 |
| 30 | 150 | 18 | 16.82; 16.61; 16.85 | 8.92; 7.83; 9.17 | 0.52 |
|   | 300 | 9 | 15.18; 13.80; 13.12 | 6.87; 6.61; 6.80 | 0.48 |
| 100 | 150 | 18 | 15.94; 15.95; 18.09 | 7.48; 8.06; 6.72 | 0.45 |
|   | 300 | 9 | 15.33; 12.34; 14.45 | 5.77; 5.27; 6.21 | 0.41 |
| 1000 | 150 | 18 | 18.26; 16.92; 17.93 | 6.26; 5.36; 5.50 | 0.32 |
|   | 300 | 9 | 14.14; 13.29; 15.41 | 5.53; 6.13; 4.23 | 0.37 |

The results demonstrate that the subject method and apparatus provide for a simple and accurate method for determining the presence of an analyte in a medium, either qualitatively or quantitatively. Greatly enhanced accuracy in the determination is obtained by having a calibration surface which provides a signal and is subject to the same influences and fluctuations as the production of the signal at the surface dependent upon the analyte concentration. Thus, one is able to visually determine the presence of an analyte above a predetermined level or by employing ratios of the signal level from each of the surfaces, one can quantitate the observed results in relation to ratios obtained with known amounts of the analyte and graphing the change in ratio of signal level with change in concentration.

The subject method and apparatus provide for numerous advantages in employing competitive protein binding assays, where the protocols are simple, rapid, and can be performed by relatively unsophisticated personnel. Furthermore, the methods involve few steps and provide for a built-in safety factor, in that errors other than the measurement of the analyte sample will affect the measurement surface and calibration surface comparably. Thus, the error will in effect cancel.

Although the foregoing invention has been described in some detail by way of illustration and example for purposes of clarity of understanding, it will be obvious that certain changes and modifications may be practiced within the scope of the appended claims.

What is claimed is:

1. In a method for determining the presence in a sample of an analyte, which analyte is a member of a specific binding pair ("mip") consisting of ligand and receptor ("antiligand"), said method employing a signal producing system having at least two enzymes, including one enzyme bound to a mip ("enzyme-bound-mip"), and a solute dye precursor which is catalytically transformed to an insoluble dye by one of said enzymes bound to a mip-containing measurement first surface, said insoluble dye producing a change in a detectable signal at said first surface in proportion to the amount of analyte, where said mip at said first surface provides for binding of enzyme-bound-mip through mip complex formation to said first surface, and contacting of said first surface with said sample and said enzyme-bound-mip results in binding of said enzyme-bound-mip to said first surface in proportion to the amount of analyte in said sample, the improvement which comprises:

during said contacting, having adjacent to said first surface, a calibration second surface to which anti-enzyme receptor is bound in a predetermined amount and to which enzyme of said enzyme-bound-mip becomes bound through mip complex formation in an amount which provides substantially predetermined ratios to the amount of enzyme-bound-mip bound to said first surface, whereby the ratio of the change in signal at said second surface to the change in signal at said first surface defines the amount of analyte in said sample substantially independent of non-specific factors.

2. In a method for determining the presence in a sample of an analyte, which analyte is a member of a specific binding pair ("mip") consisting of ligand and receptor ("antiligand"), said method employing a signal producing system having at least two enzymes, including one enzyme bound to a mip ("enzyme-bound-mip"), wherein a second ligand other than the ligand analyte is bonded to said enzyme, and a solute dye precursor which is catalytically transformed to an insoluble dye by one of said enzymes bound to a mip-containing measurement first surface, said insoluble dye producing a change in a detectable signal at said first surface in proportion to the amount of analyte, where said mip at said first surface provides for binding of enzyme-bound-mip through mip complex formation to said first surface, and contacting of said first surface with said sample and said enzyme-bound-mip results in binding of said enzyme-bound-mip to said first surface in proportion to the amount of analyte in said sample, the improvement which comprises:

during said contacting, having adjacent to said first surface, a calibration second surface to which anti (second ligand) receptor is bound and to which enzyme of said enzyme-bound-mip becomes bound through mip complex formation in an amount which provides substantially predetermined ratios to the amount of enzyme-bound-mip bound to said first surface, whereby the ratio of the change in signal at said second surface to the change in signal at said first surface defines the amount of analyte in said sample substantially independent of non-specific factors.

3. A method according to claim 2, wherein said second ligand is conjugated to an enzyme molecule other than enzyme-bound-mip.

4. A method according to claim 2, wherein said second ligand is conjugated to the same enzyme molecule as said enzyme-bound-mip.

* * * * *